United States Patent
Pruter et al.

(10) Patent No.: US 8,747,324 B1
(45) Date of Patent: *Jun. 10, 2014

(54) METHOD AND DISPOSABLE APPARATUS FOR GUIDING NEEDLES

(75) Inventors: Rick L. Pruter, Iowa City, IA (US); Quanah Lee Bain, Cedar Rapids, IA (US)

(73) Assignee: Protek Medical Products, Inc., Iowa City, IA (US)

( * ) Notice: Subject to any disclaimer, the term of this patent is extended or adjusted under 35 U.S.C. 154(b) by 2505 days.

This patent is subject to a terminal disclaimer.

(21) Appl. No.: 10/709,933

(22) Filed: Jun. 7, 2004

Related U.S. Application Data

(62) Division of application No. 10/065,029, filed on Sep. 11, 2002, now Pat. No. 6,758,817.

(51) Int. Cl.
*A61B 8/14* (2006.01)

(52) U.S. Cl.
USPC ........... 600/464; 600/459; 600/461; 604/174; 24/327

(58) Field of Classification Search
USPC ............ 600/452, 461, 462; 24/327, 557, 499, 24/331; 248/689, 229.13, 229.15; 604/116, 174, 178, 205, 240, 242, 243, 604/263, 273
See application file for complete search history.

(56) References Cited

U.S. PATENT DOCUMENTS

| | | |
|---|---|---|
| 2,451,183 A | 6/1947 | Tantimonaco |
| 2,536,963 A | 1/1951 | Stephens |
| 3,017,887 A | 1/1962 | Heyer |
| 3,302,648 A * | 2/1967 | Nelson .......................... 606/158 |
| 3,538,915 A | 11/1970 | Frampton et al. |
| 3,556,079 A | 1/1971 | Omizo |
| 4,029,084 A | 6/1977 | Soldner |
| 4,058,114 A | 11/1977 | Soldner |
| 4,108,165 A | 8/1978 | Kopp et al. |
| 4,132,496 A | 1/1979 | Casto |
| 4,249,539 A | 2/1981 | Vilkomerson et al. |
| 4,289,139 A | 9/1981 | Enjoji et al. |
| 4,332,248 A | 6/1982 | DeVitis |
| 4,363,326 A | 12/1982 | Kopel |
| 4,402,324 A | 9/1983 | Lindgren et al. |
| 4,408,611 A | 10/1983 | Enjoji |
| 4,469,106 A | 9/1984 | Harui |
| 4,489,730 A | 12/1984 | Jingu |
| 4,491,137 A | 1/1985 | Jingu |

(Continued)

FOREIGN PATENT DOCUMENTS

| | | | |
|---|---|---|---|
| WO | WO 99/34735 | 7/1999 | |
| WO | WO 01/62153 | * 8/2001 | ............... A61B 8/00 |

OTHER PUBLICATIONS

"Endocavity Needle Guide Kits" brochure of Civco Medical Instruments, © 2000, Solutions for Imaging.

(Continued)

*Primary Examiner* — Emily Schmidt
(74) *Attorney, Agent, or Firm* — Simmons Perrine Moyer Bergman PLC

(57) ABSTRACT

An apparatus and method for guiding a needle in conjunction with a biopsy using a medical imaging device, where a non-reusable needle guide, which is relatively inexpensive which grasps the sheathed bracket firm, and holds the same in a set position based upon a bullet-nose lock.

10 Claims, 6 Drawing Sheets

(56) References Cited

U.S. PATENT DOCUMENTS

| | | |
|---|---|---|
| 4,497,325 A | 2/1985 | Wedel |
| 4,504,269 A | 3/1985 | Durand |
| 4,542,747 A | 9/1985 | Zurinski et al. |
| 4,567,896 A | 2/1986 | Barnea et al. |
| 4,635,644 A | 1/1987 | Yagata |
| 4,742,829 A | 5/1988 | Law et al. |
| 4,781,067 A | 11/1988 | Cichanski |
| 4,838,506 A | 6/1989 | Cooper |
| 4,865,590 A | 9/1989 | Marmar |
| 4,877,033 A | 10/1989 | Seitz, Jr. |
| 4,883,059 A | 11/1989 | Stedman et al. |
| 4,898,178 A | 2/1990 | Wedel |
| 4,899,756 A | 2/1990 | Sonek |
| 4,911,173 A | 3/1990 | Terwilliger |
| 4,970,907 A | 11/1990 | Flynn |
| 5,052,396 A | 10/1991 | Wedel et al. |
| 5,076,279 A | 12/1991 | Arenson et al. |
| 5,088,178 A | 2/1992 | Stolk |
| 5,088,500 A | 2/1992 | Wedel et al. |
| 5,161,764 A | 11/1992 | Roney |
| 5,235,987 A | 8/1993 | Wolfe |
| 5,343,865 A | 9/1994 | Gardineer et al. |
| D362,064 S | 9/1995 | Smick |
| 5,469,853 A | 11/1995 | Law et al. |
| 5,623,931 A | 4/1997 | Wung et al. |
| D383,968 S | 9/1997 | Bidwell et al. |
| 5,758,650 A | 6/1998 | Miller et al. |
| 5,871,448 A | 2/1999 | Ellard |
| 5,910,113 A | 6/1999 | Pruter |
| 5,924,992 A | 7/1999 | Park et al. |
| 5,941,889 A | 8/1999 | Cermak |
| 5,968,016 A | 10/1999 | Yerfino et al. |
| D424,693 S | 5/2000 | Pruter |
| 6,095,981 A | 8/2000 | McGahan |
| 6,102,867 A | 8/2000 | Dietz et al. |
| 6,139,544 A | 10/2000 | Mikus |
| 6,203,499 B1 | 3/2001 | Imling et al. |
| 6,296,614 B1 | 10/2001 | Pruter |
| 6,311,084 B1 | 10/2001 | Cormack et al. |
| 6,361,499 B1 | 3/2002 | Bates et al. |
| 6,371,968 B1 | 4/2002 | Kogasaka et al. |
| 6,758,817 B1 | 7/2004 | Pruter |
| 2001/0034530 A1 | 10/2001 | Malackowski et al. |

OTHER PUBLICATIONS

"Cicvoscan, Product News and Special Offers From Civco" Brochure of Civco Medical Instruments, Winter 2001.

* cited by examiner

METHOD AND DISPOSABLE APPARATUS FOR GUIDING NEEDLES

CROSS REFERENCE TO RELATED APPLICATIONS

This application is a divisional application of application Ser. No. 10/065,029 filed on Sep. 11, 2002, entitled "METHOD AND DISPOSABLE APPARATUS FOR GUIDING NEEDLES" by the same inventors and assigned to the same assignee, which application is incorporated in its entirety by this reference.

BACKGROUND OF INVENTION

In recent years, handheld medical imaging transceivers, such as ultrasound and gamma ray transceivers, have been used extensively for various medical imaging situations.

In the past, the physician or medical professional typically will cover an ultrasound transceiver with a sterile sheath. Usually under the sheath is a mounting bracket attached to the transceiver. A needle guide is then typically attached over the sheath and coupled to the underlying bracket.

While these needle guides have been used extensively in the past, they do have some drawbacks. First of all, these needle guides require considerable attention and hand-to-eye coordination to be properly used. Additionally, these types of needle guides are often relatively expensive.

Consequently, there exists a need for improved methods and apparatus for guiding needles in an efficient manner.

SUMMARY OF INVENTION

It is an object of the present invention to provide an apparatus and method for guiding a needle in an efficient manner.

It is a feature of the present invention to include a plastic spring-like member.

It is another feature of the present invention to include, on the front side of the needle path, an enlarged base for guiding a needle into a grasping mechanism.

It is another feature of the present invention to include an enlarged base on a backside of the needle path for protecting the sheath from puncture by the moving needle.

It is another feature of the present invention to include a base-to-bracket attachment mechanism which is adapted for positive attachment to the bracket with a predetermined grasping force in a non-reusable manner.

It is an advantage of the present invention to achieve improved efficiency in guiding needles.

The present invention is an apparatus and method for guiding needles, designed to satisfy the aforementioned needs, provide the previously stated objects, include the above-listed features, and achieve the already articulated advantages. The present invention is carried out in a "physician burden-less" manner in a sense that the burden on a physician or other medical professional in guiding needles during the process of insertion into the needle guide, has been greatly reduced. Additionally, the system is carried out in an inexpensive manner in the sense that the use of plastic members for providing spring biasing for a needle grasping member is used to replace expensive metal springs. Finally, the present invention is carried out in a disposable manner in the sense that the base and the clamp used to couple to the sheathed bracket are designed to be used only once and then discarded.

Accordingly, the present invention is an apparatus and method including a needle guide with a plastic biasing member, enlarged base portions, and base-to-bracket locks which are non-reusable.

BRIEF DESCRIPTION OF DRAWINGS

The invention may be more fully understood by reading the following description of the preferred embodiments of the invention, in conjunction with the appended drawings wherein.

DETAILED DESCRIPTION

Figure 1:
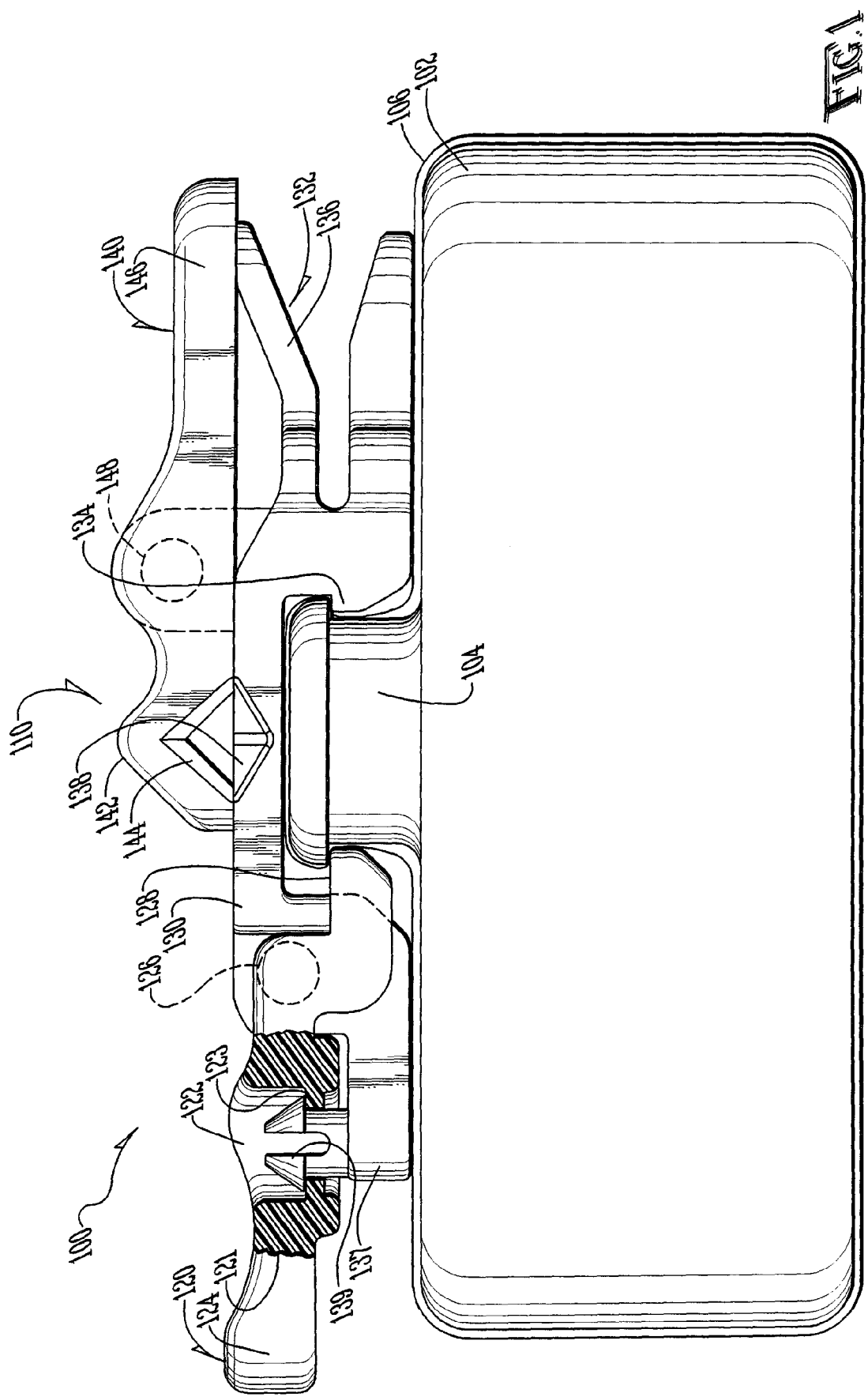
FIG. 1 is a partial cut-away side view of the apparatus of the present invention in a closed orientation.

Now referring to the drawings wherein like numerals refer to like matter throughout, and more specifically referring to FIG. 1, there is shown a needle guide, bracket and medical imaging transceiver system of the present invention generally designated 100. The system 100 includes a medical imaging transceiver 102 which could be any type of imaging system or device, and a transceiver bracket 104 which is coupled to said medical imaging transceiver 102 for the purpose of facilitating coupling with needle guides and other instruments. Transceiver bracket 104 can be coupled to medical imaging transceiver 102 in any suitable manner, such as clamps, screws, adhesive, etc. Transceiver/bracket covering sterile sheath 106 is disposed about transceiver bracket 104 and medical imaging transceiver 102 in a well-known manner. Needle guide assembly 110 is shown having a movable base portion 120, stationary base portion 130 and a needle grasping member 140, all of which could be made of any suitable material; however, a plastic material is preferred.

Movable base portion 120 includes a bullet-nose receiving hole 122 therein which, when viewed through the cut-away portion outlined by cut-away line 121, includes a bullet-nose removal inhibitor surface 123. Movable base portion 120 also includes a movable base handle end 124 which pivots about movable base pivot point 126. On an opposing end from movable base handle end 124 is movable base bracket grasping surface 128, which is configured to grasp a surface of transceiver bracket 104 when movable base handle end 124 is disposed in a closed and locked orientation.

Needle guide assembly 110 includes stationary base portion 130, which includes a stationary base biasing portion 132, which has a stationary base bracket mating portion 134 and a stationary base spring biasing member 136. Stationary base spring biasing member 136 is configured to provide a biasing force on needle grasping member 140. Stationary base portion 130 further includes a stationary lock end 137 having a bullet-nose lock male member 139. Bullet-nose lock male member 139 are well known in the art for providing positive attachment between items in a manner that separation of the items results in a destruction of the future capability of the bullet-nose lock male member 139 to firmly attach the items, which mates with bullet-nose removal inhibitor surface 123 of bullet-nose receiving hole 122 in movable base portion 120. Stationary base portion 130 further includes a stationary base needle entrance-guiding channel 138 disposed along an outside top edge of stationary base portion 130.

Disposed above stationary base portion 130 is needle grasping member 140, which has a needle grasping end 142 with a needle receiving void 144 therein disposed in axial alignment with stationary base needle entrance-guiding channel 138, so that a needle can be simultaneously in both stationary base needle entrance-guiding channel 138 and needle receiving void 144. Needle grasping member 140 includes a needle grasping member handle end 146, which when depressed toward stationary base biasing portion 132, causes needle grasping end 142 to pivot about needle grasping member pivot point 148. Stationary base spring biasing member 136 provides a resisting force upon needle grasping member handle end 146, which urges needle grasping end 142 into contact with stationary base portion 130.

Figure 2:
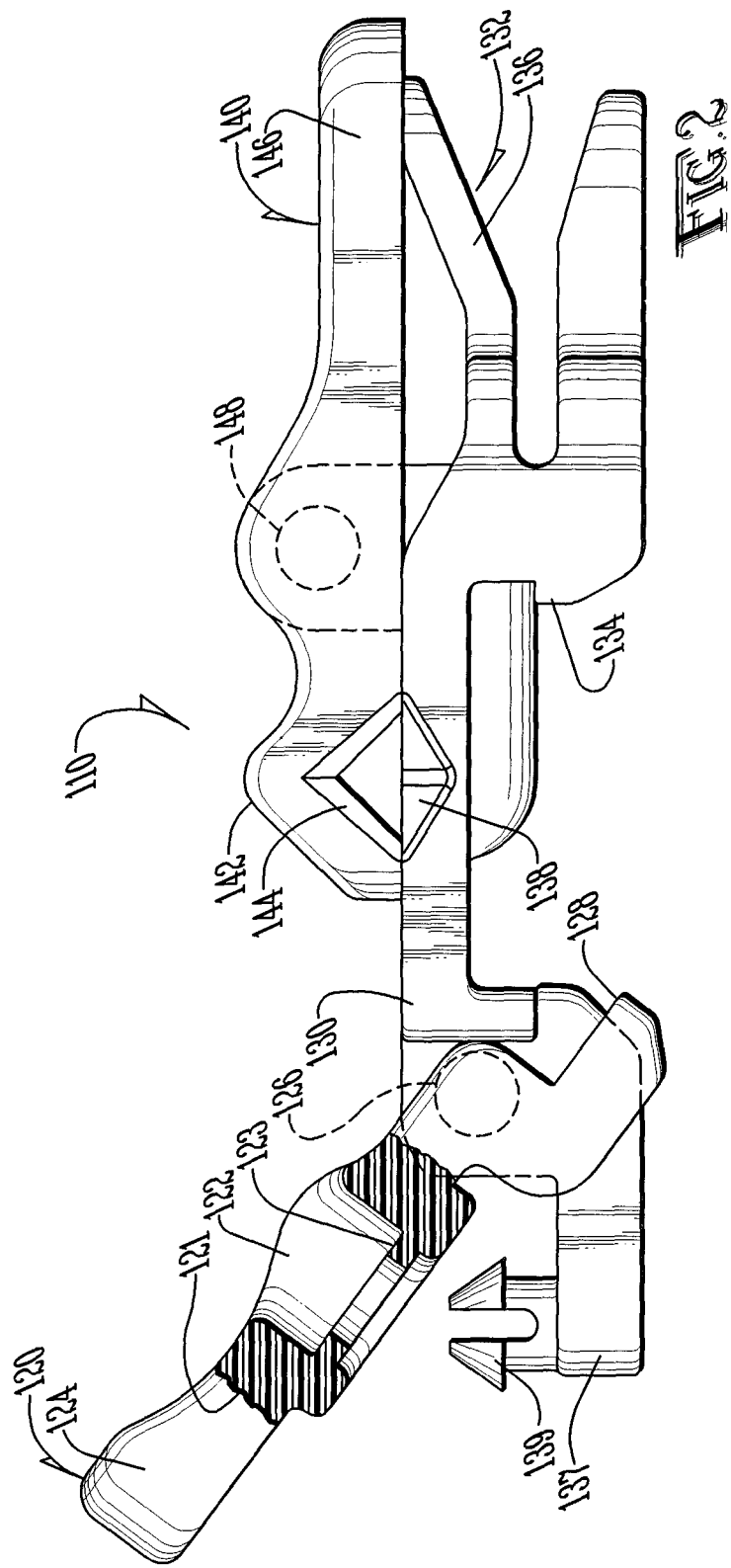
FIG. 2 is a side view of the needle guide of FIG. 1, in an open orientation prior to closing.

Now referring to FIG. 2, there is shown needle guide assembly 110 of FIG. 1 wherein movable base portion 120 is oriented in an open position prior to being closed and locked.

Figure 3:
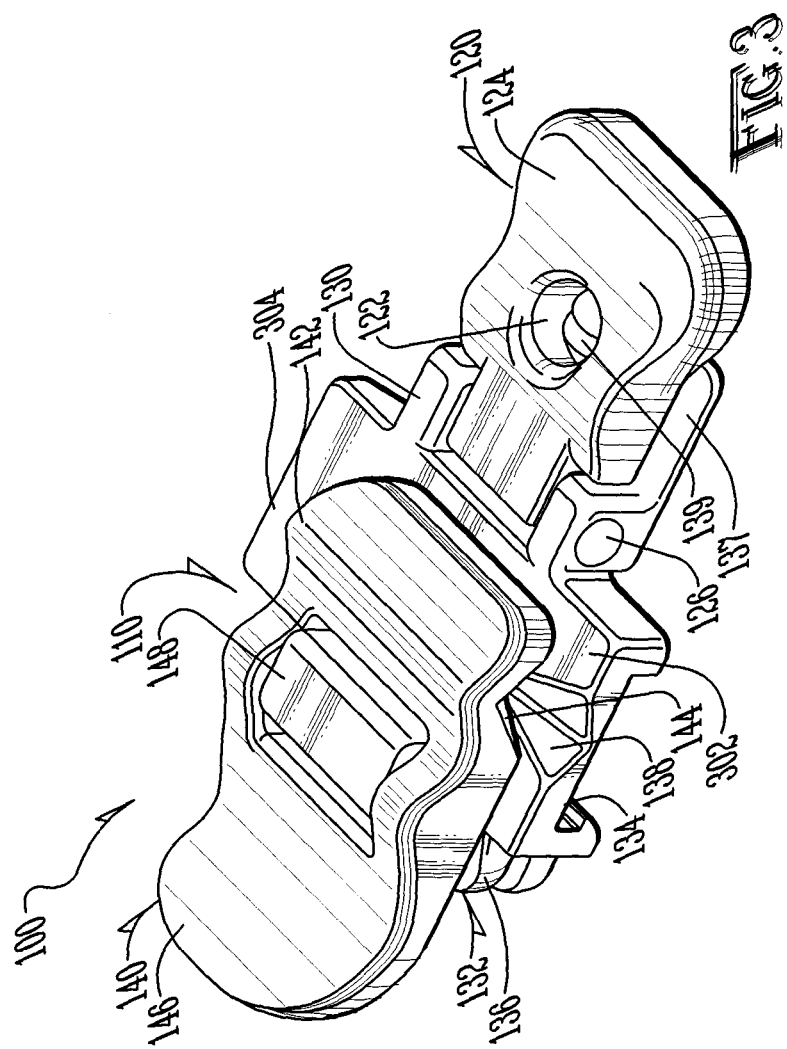
FIG. 3 is a perspective view of a needle guide of FIG. 2, which has a top enlarged sheath puncture protecting area and a bottom enlarged sheath puncture protecting area.

Now referring to FIG. 3, there is shown a perspective view of the needle guide assembly 110 of FIG. 2. Stationary base portion 130 is shown having a top enlarged sheath puncture protecting area 302 and a bottom enlarged sheath puncture protecting area 304. Top enlarged sheath puncture protecting area 302 and bottom enlarged sheath puncture protecting area 304 may be optional features, depending upon the particular needs of a particular application. Since the transceiver/bracket covering sterile sheath 106 (FIG. 1) is disposed adjacent to stationary base portion 130, the top enlarged sheath puncture protecting area 302 and the bottom enlarged sheath puncture protecting area 304 perform the functions of shielding transceiver/bracket covering sterile sheath 106 from puncture at a location of transceiver/bracket covering sterile sheath 106 where risk of puncture by the needle during insertion is highest. In a preferred embodiment, top enlarged sheath puncture protecting area 302 and bottom enlarged sheath puncture protecting area 304 extend at least one-fourth (¼) of an inch beyond the needle grasping member. In a most preferred embodiment of the present invention, top enlarged sheath puncture protecting area 302 extends at least three-eighths (⅜) of an inch beyond the needle grasping member 140.

Figure 4:
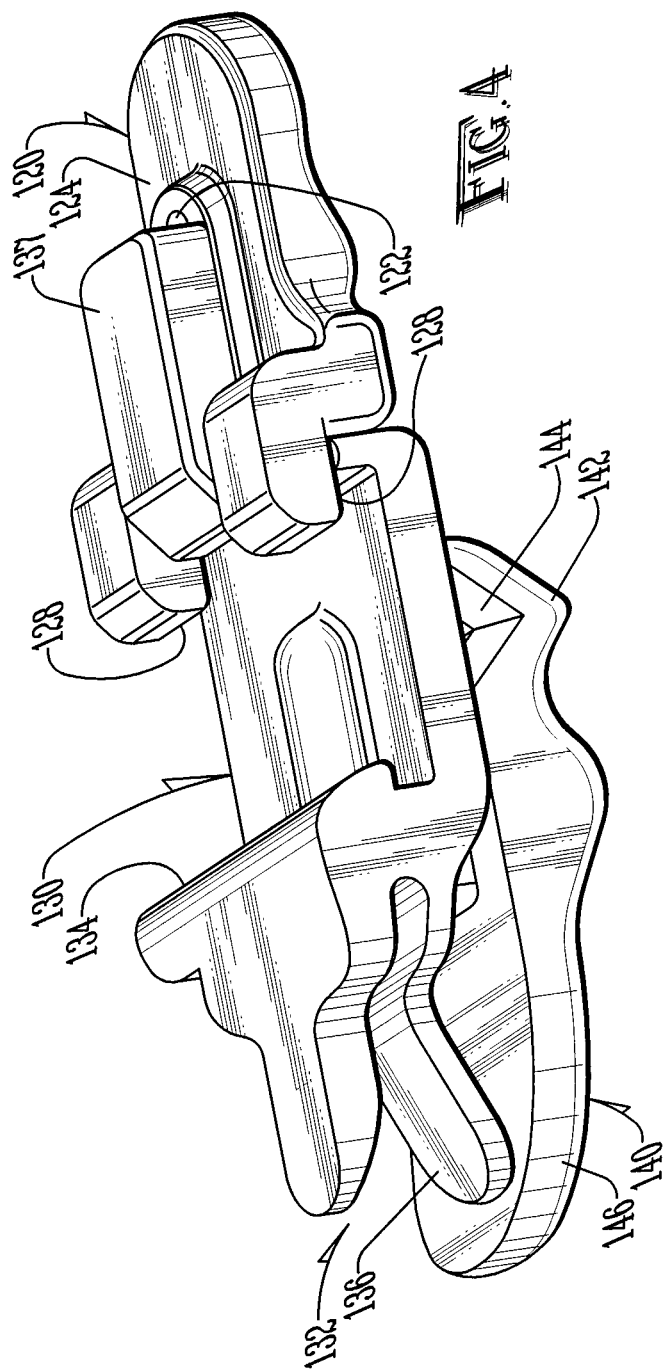
FIG. 4 is a perspective view of the reverse side of the needle guide of FIG. 1.

FIG. 4 is a perspective view of the reverse side of the needle guide of FIG. 1, in a closed and locked position.

Figure 5:
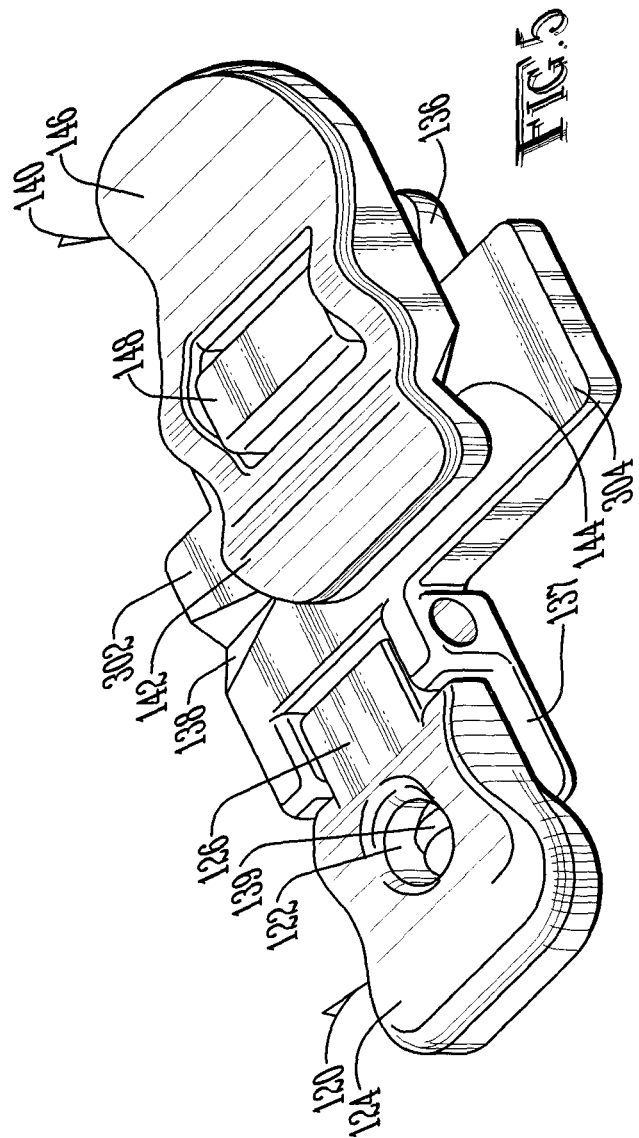
FIG. 5 is a perspective view of an alternate embodiment of the needle guide of the present invention, which is configured to mate with a bracket different from the bracket depicted in FIG. 1.

FIG. 5 is a perspective view of an alternate embodiment of the present invention where the components labeled the same as in FIGS. 1-4 are similar in function, but have differing shape and orientation.

Figure 6:
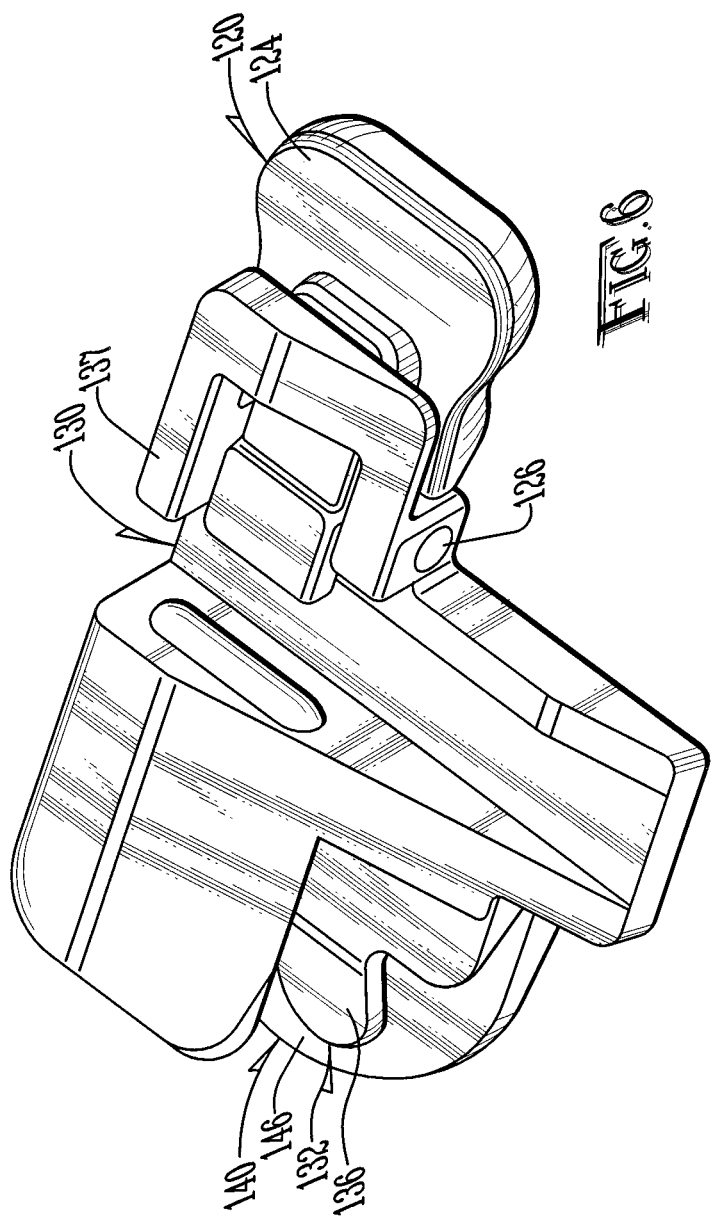
FIG. 6 is a perspective view of a reverse side of the needle guide of FIG. 5.

FIG. 6 is a reverse side of the needle guide of FIG. 5 which is obtained by rotating the device of FIG. 5 so that the opposite side of needle grasping member handle end 146 is found on the left side of the drawing.

In operation, the apparatus and method of the present invention as described and shown in FIGS. 1-3, could function as follows:

A transceiver bracket 104 is mounted on a medical imaging transceiver 102. A transceiver/bracket covering sterile sheath 106 is pulled over the medical imaging transceiver 102 and transceiver bracket 104 combination. Stationary base portion 130 is mated with transceiver bracket 104 by first engaging stationary base bracket mating portion 134 with transceiver bracket 104, and then movable base handle end 124 is pivoted so that movable base bracket grasping surface 128 contacts the sheathed transceiver bracket 104, and stationary lock end 137 is disposed adjacent the movable base handle end 124. Bullet-nose lock male member 139 is thereby inserted into bullet-nose receiving hole 122 and mates with bullet-nose removal inhibitor surface 123. A needle is placed against top enlarged sheath puncture protecting area 302 and moved into stationary base needle entrance-guiding channel 138 (wherein said needle entrance guiding structure is a V-shaped channel disposed in said top enlarged sheath puncture protecting area where an apex of said V-shaped channel is directed toward said needle retention location) where it is readily guided into needle-receiving void 144. The needle exits needle-receiving void 144, traverses bottom enlarged sheath puncture protecting area 304, and is then available for interaction with a patient. Once the procedure is finished, the needle can be removed by pressing needle grasping member handle end 146, which causes needle grasping end 142 to move from stationary base portion 130, thereby permitting disengagement of the needle from the needle guide assembly 110.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

The invention claimed is:

1. A dual push member actuated needle guide assembly comprising:

a stationary base portion configured to cooperate with a transceiver bracket; a needle grasping clamp member which is configured to pivot with respect to said stationary base portion, around a first axis;

said needle grasping clamp member having a needle grasping end and a needle grasping member handle end, which is configured to release needle retaining forces when pressed in a first direction;

a movable base portion coupled to said stationary base portion configured to contact said transceiver bracket and thereby hold said stationary base portion relative to said transceiver bracket, when said movable base portion is pressed in said first direction;

a lock disposed on one of and extending between said stationary base portion and a movable base portion coupled to said stationary base portion;

wherein said lock comprises a three-dimensionally rounded head configured to mate with a void in another of said stationary base portion and a movable base portion coupled to said stationary base portion;

wherein said movable base portion pivots around a second axis which is parallel to said first axis and orthogonal to a central axis through said three-dimensionally rounded head;

a plastic spring biasing member configured to provide a biasing force such that said needle grasping end is urged toward said stationary base portion;

wherein said plastic spring biasing member provides a biasing force on said needle grasping member handle end; and said stationary base portion is rigidly configured to contact and encircle a portion of said transceiver bracket.

2. A needle guide assembly of claim 1 wherein said plastic spring biasing member is a resilient tab coupled to said stationary base portion and configured to engage said needle grasping member handle end.

3. A needle guide assembly of claim 2 wherein said resilient tab is an integral portion of said stationary base portion.

4. A needle guide assembly of claim 2 further comprising a needle guiding structure configured to guide a needle into a location where said resilient tab provides a biasing force to retain said needle.

5. A needle guide assembly of claim 4 wherein said needle guiding structure is a finder groove in an enlarged sheath puncture protecting area.

6. A dual push member actuated needle guide assembly comprising:

a retaining structure fixed with respect to a surface on an imaging transceiver;

a rigid stationary base portion having a top enlarged sheath puncture protecting area;

a movable base portion pivotally coupled to said stationary base portion around a first axis so as to retain said stationary base portion to said retaining structure;

a lock disposed on one of and extending between said stationary base portion and said movable base portion coupled to said stationary base portion;

wherein said lock comprises a three-dimensionally rounded head coupler configured for mating with a female section of a male-to-female coupler in another of said stationary base portion and a movable base portion coupled to said stationary base portion and having a central axis which is different from said first axis;

a needle grasping member coupled to said stationary base portion, which is configured to pivot around a second axis which is parallel with said first axis and orthogonal to said central axis; and said top enlarged sheath puncture protecting area extending beyond said needle grasping member by at least one-fourth (¼) of an inch.

7. A needle guide assembly of claim 6 wherein said top enlarged sheath puncture protecting area includes a stationary base needle entrance guiding structure thereon, which is configured to guide a needle into a needle retention location where said needle grasping member provides a motion resisting force onto said needle; and said stationary base portion is rigidly configured to contact and encircle a portion of said retaining structure.

8. A needle guide assembly of claim 7 wherein said needle entrance guiding structure is a V-shaped channel disposed in said top enlarged sheath puncture protecting area where an apex of said V-shaped channel is directed toward said needle retention location.

9. A needle guide assembly of claim 8 wherein said needle retention location is defined by limits of said stationary base portion and a needle-receiving void in a needle grasping end of said needle grasping member; and said needle grasping member is a pivoting clamp.

10. A needle guide assembly of claim 9 wherein a resilient plastic tab integral with said stationary base portion provides a biasing force to cause said pivoting clamp to retain said needle in said needle-receiving void.

* * * * *